US006873152B2

(12) United States Patent
Kliman et al.

(10) Patent No.: US 6,873,152 B2
(45) Date of Patent: Mar. 29, 2005

(54) DIFFERENTIAL SENSOR APPARATUS AND METHOD FOR LAMINATED CORE FAULT DETECTION

(75) Inventors: Gerald Burt Kliman, Niskayuna, NY (US); Manoj Ramprasad Shah, Latham, NY (US); Sang-Bin Lee, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 10 days.

(21) Appl. No.: 10/248,246

(22) Filed: Dec. 30, 2002

(65) Prior Publication Data

US 2004/0124833 A1 Jul. 1, 2004

(51) Int. Cl.[7] ........................ G01N 27/82; G01R 31/34
(52) U.S. Cl. ........................ 324/241; 324/242; 324/772
(58) Field of Search ................ 324/545, 546, 324/772, 228, 232, 233, 230, 240, 242, 237, 238, 241; 318/490

(56) References Cited

U.S. PATENT DOCUMENTS

| | | | | |
|---|---|---|---|---|
| 3,247,453 | A | * 4/1966 | Quittner | 324/241 |
| 4,996,486 | A | * 2/1991 | Posedel | 324/545 |
| 5,341,095 | A | * 8/1994 | Shelton et al. | 324/772 |
| 5,365,166 | A |   11/1994 | Dailey et al. | 324/158.1 |
| 5,689,183 | A | * 11/1997 | Kohama | 324/233 |
| 5,990,688 | A | * 11/1999 | Bourgeois et al. | 324/545 |
| 6,469,504 | B1 |   10/2002 | Kliman et al. | 324/228 |
| 6,489,781 | B1 |   12/2002 | Kliman et al. | 324/545 |
| 6,636,037 | B1 | * 10/2003 | Ou-Yang | 324/240 |

FOREIGN PATENT DOCUMENTS

GB     2 044 936     10/1980

OTHER PUBLICATIONS

McNamara et al., "EL CID vs. Loop Test: Correlation of Results in Assessing Stator Core," Oct. 2002, pp. 1–2.

Sutton, J., "EL–CID—An Easy Way To Test Stator Cores," Jun. 1982, pp. 15–21.

Sutton, J., "EL CID: An Easier Way To Test Stator Cores," Jul. 1980, pp. 33–37.

Sutton et al., "Electrical Machines–Design and Applications," Jul. 1982, pp. 119–130.

Rickson, C.D., "A New Technique For Core Lamination Testing,," Sept. 1985, pp. 239–243.

Paley, D.B., "Low Power Stator Core Fault Testing Using EL CID," Aug. 1998, IEEE vol. 2, pp. 1010–1014.

Ridley, G.K., "EL CID Application Phenomena," Sep. 1993, 8 pgs.

(Continued)

*Primary Examiner*—Anjan K. Deb
(74) *Attorney, Agent, or Firm*—Nixon & Vanderhye P.C.

(57) ABSTRACT

A differential probe is scanned along a stator core tooth portion to detect lamination faults. The probe utilizes two magnetic flux injection yokes arranged side-by-side in relatively close proximity, each yoke having two arm portions and two core-tooth flux-injection surfaces, each yoke being wound with an excitation coil winding and at least one yoke-arm of each yoke having a magnetic flux sensor. Current is supplied to the excitation coil windings on each yoke to inject magnetic flux into the stator core laminations while the probe is moved in a scanning process along the core teeth across the laminations. The magnetic flux differential detected at adjacent regions in the core by flux sensors on each of the two yokes is used to incrementally evaluate the core for laminations faults. The output produced by the differential probe may be converted to a digital signal and provided to a computer system for storage and future analysis.

21 Claims, 8 Drawing Sheets

OTHER PUBLICATIONS

Ridley, G.K., "Electromagnetic Field Distortion Effects on El CID Tests," Jul. 1982, pp. 187–193.

Shelton et al., "A Comparative Analysis Of Turbogenerator Core Inspection Techniques," 1985, pp. 643–650.

Crouse et al., "Alternatives To Generator Crawl–Through Maintenance Inspection," 1987, pp. 316–320.

Sutton, J., "Theory Of Electromagnetic Testing Of Laminated Stator Cores," INSIGHT, vol. 36, No. 4, Apr. 1994, pp. 246–251.

Crouse, et al., "Consolidated Assessment: A Minimum Disassembly Inspection Program That Enhances Turbo–Generator Availability," Proceedings of the American Power Conference, vol. 51, Copyright 1989, pp. 541–545.

Ridley, G. K., "EL CID Test Evaluation, 1984–96," Power Engineering Journal, vol. 1, No. 1, Feb. 1997 pp. 21–26.

Cadwell, et al., "FAST Gen III, The Next Generation," Proceedings of the American Power Conference, vol. 58–II, 1996, pp. 1249–1255.

Fischer, et al., "Introduction And qualification Of Digital Electromagnetic Core Imperfection Detector (EL CID) Test Equipment And Associated Robotic Delivery And Inspection Systems," Proceedings of the American Power Conference, vol. 56–II, Sponsored by Illinois Institute Of Technology, Copyright 1994, pp. 1735–1742.

Paley, D.B., "Current Low Power Stator Core Testing Using EL CID," Apr. 1999, IEE Colloquium., 3 pgs.

* cited by examiner

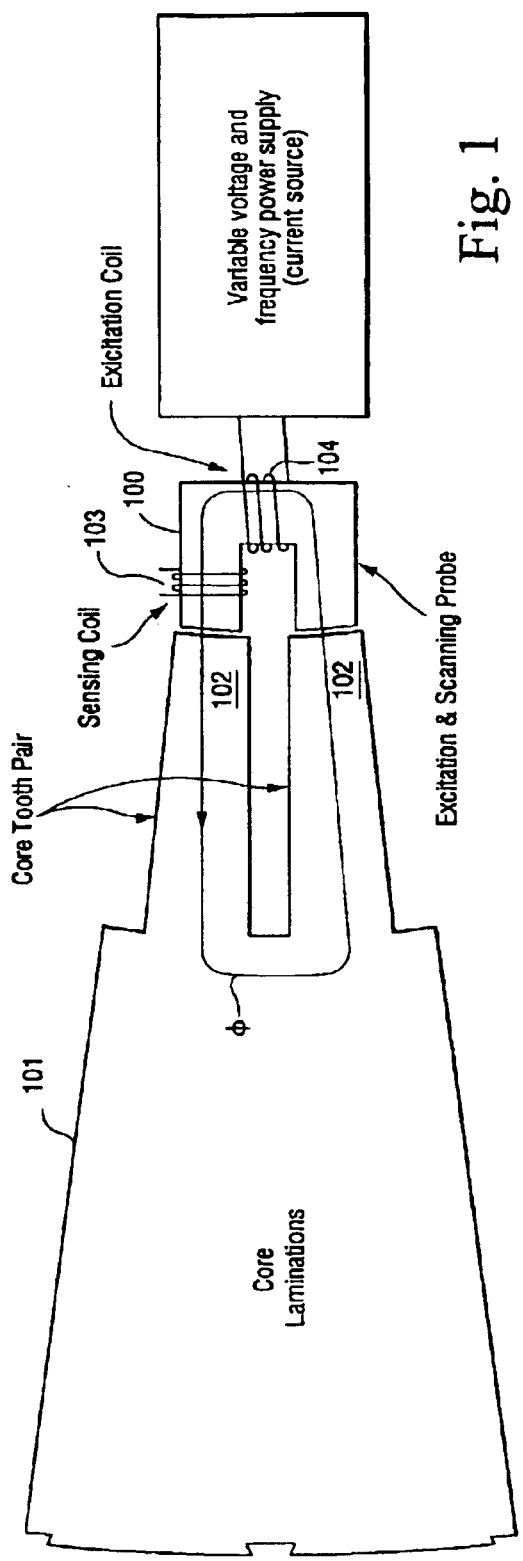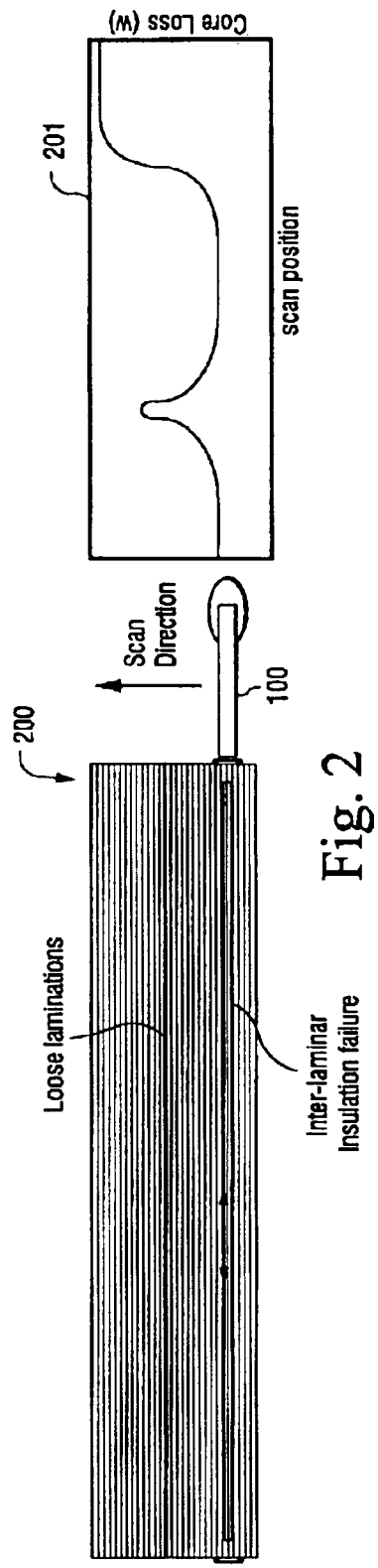
Fig. 1 PRIOR ART
Fig. 2

Testing arrangement

Interlamination short circuit detection - single yoke probe

Flux Injection Fault Test Scan - Dual yoke differential probe

DIFFERENTIAL SENSOR APPARATUS AND METHOD FOR LAMINATED CORE FAULT DETECTION

BACKGROUND OF INVENTION

The present invention relates generally to testing devices and methods and, more particularly, to a testing method and apparatus for detecting and locating faults in laminated cores of electric machines.

For the purposes of the following discussion, a lamination segment of the stator of a large generator may be considered as an example structure on which the present method and apparatus is suited for performing lamination fault testing. A conventional laminated core segment of a large generator stator includes a back iron portion, teeth and slots. Lamination segments are typically formed into a magnetic core by stacking. A plurality of lamination segments (eighteen lamination segments each being twenty degrees, as one example) may be used to form a complete first lamination layer with the next plurality of lamination segments forming a complete second lamination layer on top of and offset from the lamination segments in the first lamination layer. Such stacking continues until formation of a short stack of about 2.54 centimeters to about 10.16 centimeters thick. A plurality of short stacks are further joined and/or clamped by bolts and/or other mechanical devices to form a stator core. A typical large generator stator core may have a diameter, for example, ranging from about one meter to about three meters and a length ranging from about one meter to about ten meters.

Lamination faults in a stator core, such as short circuited laminations, may become highly destructive in large electric machines. Inter-lamination short circuits (caused by mis-operation or manufacturing defects such as burrs, defects in lamination coating, damage during assembly) cause eddy currents to flow through the shorted laminations and key bars. These currents are driven by the time varying flux in the stator core present during normal generator operation. The heating caused by these currents can cause burning and melting of the laminations at the location of the defect. The additional heating can also cause insulation degradation and failure in the stator bars. If these defects are found during the manufacturing or rewinding operations, they can be corrected. Consequently, it is desirable to have an easy and efficient method and apparatus for testing laminated stator cores for such faults accurately, within as fine a resolution as reasonably feasible. Moreover, it is also desirable to have a stator core testing apparatus and method that is easily implemented both during the manufacture of the core and during routine maintenance or service procedures of the electric machines in which such laminated cores are used.

One well known conventional stator core testing method, more commonly known as a "ring test", employs a technique of exciting the stator laminations at a rated operating induction level. The ring test relies upon the detection of eddy current heating caused by short circuit currents in the laminations. The generator stator core is specially wound with an excitation winding having a number of turns of cable in the manner of a toroid. The current level in the windings is chosen such that the flux driven in the core is near normal operating levels. Local temperature differences produced by eddy currents due to an interlamination short can be detected by an infrared scanner. Unfortunately, the ring test requires the use of a controllable high-power, high-voltage source and special stator core excitation windings with large cross sections. Short circuits that are located below the surface of the stator teeth and slots are difficult to find, since thermal diffusion causes the surface temperature rise to become diffuse. Moreover, because of the high power levels used in the ring test, personnel are not allowed in the bore of the stator core during testing. In addition, cables used in the test must be appropriately sized to accommodate the high power level which inevitably leads to long setup and removal times. These drawbacks and the high power requirements cause this method to be usually impractical for field test applications.

Another known inspection technique, such as disclosed in UK Patent 2,044,936 to Sutton, involves detecting changes in the flux fields due to interlamination shorts with weak induction. This technique is commonly referred to as an Electromagnetic Core Imperfection Detector (EL CID) test. With this test, a core stack is magnetized at a much lower magnetic flux level as compared to its rated operating level and, consequently, only a low power, low-voltage power supply is needed. Each tooth-pair is then scanned with a special detector coil system to look for anomalies in the flux. As in the ring test, a disadvantage of this testing method is that it also requires a special winding for the stator core.

In yet another approach, as described in commonly assigned U.S. Pat. Nos. 6,469,504 and 6,489,781 both to Kliman et al., stator core lamination faults are more easily and efficiently detected through the use of a flux-injection testing probe of the type, for example, as depicted in FIG. 1. This flux-injection probe testing approach, as described in the above mentioned applications, has discernable advantages as compared to prior embodiments. For example, short stacks of laminations may be tested individually while stacking during core fabrication and/or during core servicing so that, if a fault is detected, remedial measures may be performed on the affected lamination immediately rather than having to substantially disassemble a completed core to access a fault later determined to be located in the middle of the core.

However, when the thickness of a flux-injection type probe exceeds the thickness of about two or three core laminations, sensitivity and selectivity are reduced. The sensor magnetic yoke itself will influence the losses measured along the core. Unfortunately, physical and practical constraints limit the minimum feasible sensor yoke thickness. Moreover, magnetic flux sensitivity is also influenced by the distance between the magnetic yoke and the core laminations. Typically, about 50–75 micrometers of lamination stagger may result from punching tolerances and assembly variability when fabricating laminated cores. In electric machines that function as generators, lamination core stagger is typically filled in and covered up by layers of thick paint. Such paint further increases the effective gap between the magnetic yoke and the core which correspondingly reduces the effective sensitivity of the testing probe. In addition, incremental core losses due to individual lamination faults can often be quite small e.g., on the order of 1% or less. For at least the above reasons, it is very difficult to detect some small faults and, especially, small lamination faults when using known flux-injection probe devices and methods. Consequently, it would be highly desirable to have a core fault detection method and apparatus that provides a significant increase in sensitivity over the prior known art.

SUMMARY OF INVENTION

The method and apparatus disclosed herein may be used for detecting shorts between laminations and may potentially be used to detect faults as small as a single interlaminar insulation failure. Although the method and apparatus of the present invention are particularly applicable to the testing of electric machines that utilize a laminated core, such as used in the stators of large alternators and generators, they are also generally applicable to the testing of electrical motors, transformers and the like.

A testing probe comprising at least one pair of electromagnetic flux-injecting yokes is scanned along the stator core teeth, each individual yoke of the pair being basically "U-shaped" and functionally similar to a type as described in commonly assigned U.S. Pat. No. 6,469,504 to Kliman et al. Each yoke of the probe is arranged parallel to the other in an "upper/lower" (or "side-by-side") relationship in relatively close proximity as illustrated, for example, in FIG. 3. Each yoke includes at least two arm portions terminating in a flat core-tooth facing surface and each is wound with an excitation coil for inducing/injecting magnetic flux into the stator core laminations. The amount of flux loss experienced within the core is then measured by a flux sensor mounted on each yoke. At least one arm portion of each yoke includes a magnetic flux sensor for measuring the injected flux. With the parallel yoke arrangement of the present invention, core losses experienced at adjacent regions of a stator core may be incrementally measured and compared continuously along the stator core tooth.

An averaged product of the flux-injecting excitation coil drive current and the measured flux differential detected between the yoke pair yields a qualitative value for the incremental core loss experienced at a particular position along the core tooth due to an existing lamination fault (the product yields nothing if no fault exists at that point along the core tooth). Since core lamination fault detection resolution is limited predominantly by lamination stagger and detection probe misalignments, the ratio of the signal to background noise measured by the probe may be increased by an order of magnitude or more using this dual-yoke differential probe arrangement.

In one example embodiment of the present invention, probe manufacturing costs may be lowered and precision further enhanced by coupling the magnetic flux inducing excitation coils for each yoke in a magnetic series-aiding configuration and coupling the flux sensor coils from each yoke in a magnetic series-bucking arrangement. Construction of an embodiment of the invention may also be simplified and manufacturing cost further reduced by using a single flux-inducing excitation coil that is wound around both yokes of the probe.

In yet another example embodiment of the present invention, manufacturing the probe apparatus may be even further simplified by using a thin planar flux sensor coil positioned on one or more of the two flat flux-injecting core-tooth facing surfaces of a yoke arm in a manner similar, for example, to the arrangement of planar flux sensors as disclosed in commonly assigned U.S. Pat. No. 6,489,781 to Kliman et al. However, in contrast to that arrangement, one example embodiment of the present invention utilizes a planar flux sensor that extends substantially the full width of the core tooth and the full thickness of the flux injection surface of the yoke. Moreover, in present example embodiment, the planar flux sensor may consist of one or more planar coils and the flux sensor for each yoke of the probe are preferably connected electrically in a series-bucking magnetic arrangement.

BRIEF DESCRIPTION OF DRAWINGS

The features of the invention believed to be novel are set forth with particularity in the appended claims. The invention itself, however, both as to organization and method of operation, together with further aspects and advantages thereof, may best be understood by reference to the detailed description taken in conjunction with the following drawings, where like numerals represent like components, in which:

FIG. 1 is a diagrammatic representation of a prior art single-yoke flux injection probe and testing arrangement for testing a laminated stator core;

FIG. 2 is side view cut-away diagram of the testing arrangement of FIG. 1;

DETAILED DESCRIPTION

Figure 3:
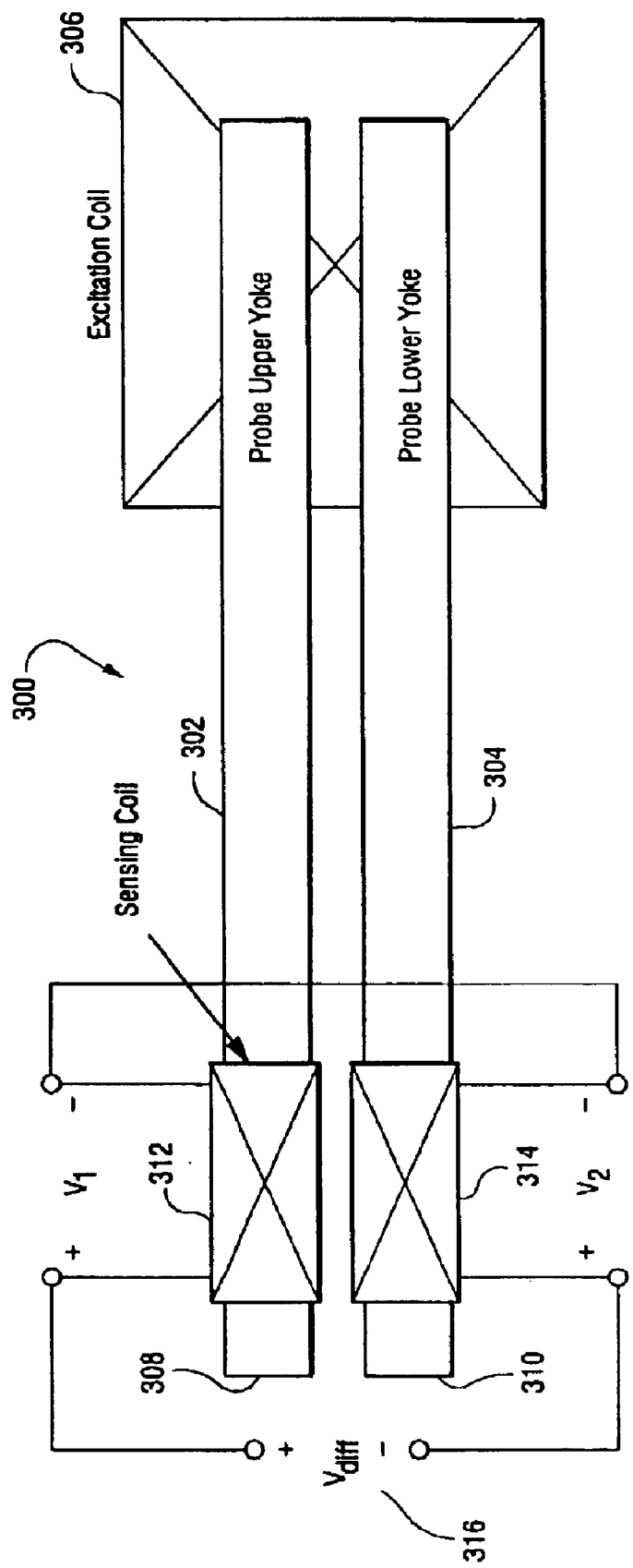
FIG. 3 is a side view diagram of one dual-yoke differential probe of the present invention.

FIG. 1 illustrates the basic flux-injection test concept of the present invention that is used for detecting core lamination faults. An example testing arrangement of the type conventionally used for performing a flux-injection test on the laminated core of an electrical machine is shown. The flux-injection probe consists of a single U-shaped ferromagnetic yoke 100 (which itself may be comprised of laminated sheets) wound with a magnetic flux generating "excitation coil" winding 104. During the testing procedure, the probe is preferably positioned in very close proximity to at least one stator core tooth pair and the excitation coil winding is supplied with an electrical current to inject a magnetic flux ($\phi$) into the stator core laminations. A flux sensing coil (flux sensor) 103 is wound on an arm of the yoke to provide a signal for detecting core lamination faults by calculating a measure of the losses experienced within the core (i.e., core loss). Basically, electromagnetic probe 100 magnetically excites core laminations by injecting a magnetic flux, $\phi$, into the core laminations 101 through a pair of core tooth projections 102. A flux sensing coil 103 on one arm of the probe yoke is used to measure an injected magnetic flux and the measured loss due to the core laminations is used as a fault indicator. In practice, a product of the measured magnetic flux and excitation current is used.

In this type of flux-injection testing, when a small portion of the core is magnetically excited, the flux response to an excitation current delivered to the excitation coil winding will be primarily due to the magnetically permeable core material as modified by normal hysteresis losses and eddy currents in the laminations, assuming the laminations are well insulated from each other. However, if faults exist anywhere in the magnetically excited region, circulating currents will be induced which will alter the magnitude and phase of the response. Such altered phases or magnitudes may be used as an indicator of core condition when one region of the core is compared against another or, alternatively, to trend a single region of the core over time or excitation amplitude. Additionally, analysis of the signal distribution for normal conditions and known fault conditions can be used to interpret measured signals in order to estimate core condition.

In general, there are four types of magnetic flux power losses (core loss) which may be experienced within a laminated core: (1) hysteresis loss, (2) eddy current loss, (3) rotational loss, and (4) small anomalous losses. (In present technique, there is no rotational loss and the anomalous loss is neglected.) Different types of inter-lamination failures within the stator core will result in an increase in at least one of the above types of magnetic flux losses.

FIG. 2 shows a side view diagram of the example testing arrangement of FIG. 1. In this example, a flux injection probe is used in a scanning test arrangement over a portion of a laminated stator core. As the flux injection probe 100 is moved in a scanning direction along the surface of a laminated core tooth, the core loss and excitation current signal obtained using the flux sensing coil may be monitored or recorded and used to provide an indication of the location and type of lamination fault as indicated by the corresponding graph 201 showing core loss vs. scan position.

In the present invention, the single-yoke flux injection probe of the prior art is replaced with a dual-yoke flux injection probe device which permits measurement of the differential flux between two adjacent positions along the core. This dual-yoke differential probe arrangement allows for the injection and accurate measurement of magnetic flux differential between laminar regions of the stator core. Core losses experienced at closely spaced adjacent regions of a stator core may be measured and compared continuously along the stator core.

FIG. 3 provides a side view diagrammatic illustration of an example dual yoke flux injection differential probe of the present invention. In this example embodiment, differential probe 300 consists of an upper yoke arm portion 302 and a lower yoke arm portion 304 fixed in a parallel arrangement in relatively close proximity to each other. Current is supplied to series connected excitation coil windings 306 on each yoke (not explicitly illustrated in FIG. 3) to inject magnetic flux into the stator core laminations from flux injection end surfaces 308 and 310. In an alternative embodiment, excitation coil windings 306 may comprise a single excitation coil wound about both upper yoke 302 and lower yoke 304, as shown in FIG. 3.

At least one arm portion of each yoke 302 and 304 includes a magnetic flux sensor 312/314 for measuring the injected magnetic flux. In this manner, the amount of core loss experienced at adjacent regions of the stator core may be incrementally measured and compared continuously while the probe is moved or scanned along a pair of stator core teeth. In the example embodiment illustrated from a side view in FIG. 3, upper yoke 302 and lower yoke 304 both include an arm portion terminating in flat core-tooth facing surfaces 308 and 310, and each arm portion is wound with separate flux sensor windings 312 and 314 for detecting magnetic flux in the stator core laminations. In a preferred example embodiment of the present invention, flux sensor windings 312 are electrically connected in a series-bucking arrangement with flux sensor windings 314 such that a differential signal is produced at flux sensor pair output 316.

Figure 4:
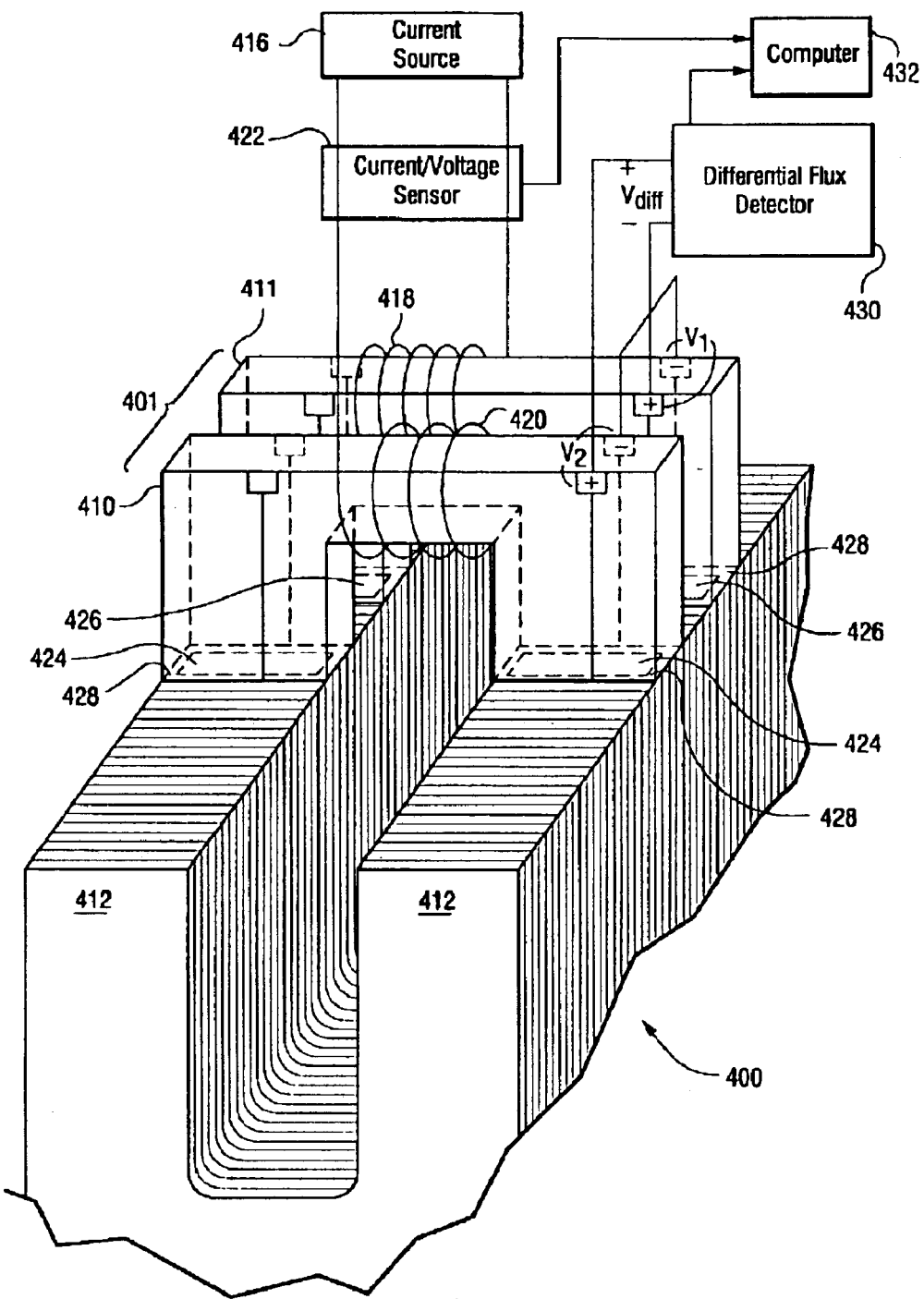
FIG. 4 is a perspective view of an example testing arrangement using the differential probe of the present invention.

FIG. 4 shows a perspective view of the differential probe of the present invention as used in an example testing arrangement for evaluating a core stack for lamination faults. In the illustrated arrangement, differential probe 401 is scanned along the surface of a tooth pair 412 of core stack 400. Laminations of core stack 400 are evaluated for faults by positioning the flux injecting end of differential probe 401, comprising magnetic yoke pair 410 and 411, in close proximity and in alignment with the top surfaces of a pair of core teeth 412. As shown, individual magnetic flux inducing excitation windings 418 and 420 are wound on each yoke of differential probe 401. A current source 416 supplies an electrical current to excitation windings 418 and 420 of probe yokes 410 and 411 to inject a magnetic flux into laminated core teeth 412. In the illustrated embodiment, excitation windings 418 and 420 are electrically connected in series in a manner such that the individual magnetic fields generated by each yoke are of the same polarity (series-aiding configuration). Alternatively, a single excitation coil could be wound about both yokes of differential probe 401. In this example embodiment of the invention, the injected magnetic flux may be significantly less than the rated operating flux levels for the core and, hence, current source 416 may be provided by using smaller, lower power and more portable equipment than traditionally required for conventional ring test arrangements.

Referring again to FIG. 4, at least one arm portion of each yoke includes a magnetic flux sensor for measuring the amount of magnetic flux coupled into a narrow region of core lamination for each yoke. In this example embodiment, flux sensing coils 312 and 314 (FIG. 3) each comprise at least one planar coil 424 and 426, and each magnetic yoke 410 includes flat core-facing surfaces 428 with the planar flux sensing winding being situated on at least one core-facing surface 428 of each yoke. One advantage of using a planar coil is that such coils may be fabricated as thin films or, for example, conductive traces printed on the surface of a substrate such as a Mylar™ sheet. Such planar coils can be fabricated by standard metallization and patterning techniques using conventional printed circuit fabrication techniques.

In the example embodiment depicted by FIG. 4, planar coil flux sensors 424, 426 are present on core-facing surfaces 428 of a differential probe yoke pair 401, which is positioned directly on/above teeth 412 of laminated core 400. In a preferred example embodiment of the present invention, planar flux sensors 424 and 426 extend substantially the full width of core tooth 412 and the full thickness of flat flux injection surface of the yoke. In addition, each planar flux sensor 426–428, may consist of one or more planar coils. At least one pair of flux sensors that are mounted at the flux-injecting end of adjacent arm potions of yokes 410 and 411, for example, planar sensors 424 and 426, are electrically connected in series in a bucking arrangement with respect to each other. In this manner, the electrical output of the series connected flux sensor pair (424, 426) produces a differential voltage output, $V_{diff}$, being the difference between individual sensor voltages $V_1$ and $V_2$. Differential flux detector 430 is connected to the series connected flux sensor pair to convert the measured differential signal, $V_{diff}$, to a digital signal for providing to computer 432. Likewise, current sensor 422 converts an excitation coil driving current supplied by current source 416 to a digital signal for providing to computer 432 for storage and analysis. An averaged product of the flux-injecting excitation coil drive current measured by current sensor 422 and the measured flux differential detected by differential flux detector 430 is computed by computer 432. This averaged product provides a qualitative value of the incremental core loss experienced at the particular position of the probe along the core tooth.

The pair of flux sensors used for providing the $V_{diff}$ signal may be located at either end of the yoke arm portions of yoke pair, as long as each sensor of the pair is on a different but adjacent yoke. In an alternative embodiment, two pairs of flux sensors, from opposite yoke arm end portion of probe 401, may used together to provide a stronger $V_{diff}$ signal. Other embodiments are also envisioned using multiple (i.e., more than two) planar coil flux sensor pairs mounted on two or more flux-inducing yoke pairs and connected so as to provide one or more differential flux signal outputs. For example, although the flux sensing arrangement of FIG. 4 shows differential flux detector 430 connected only to a single pair of flux sensors 424 and 426, a differential flux signal may be obtained from a corresponding pair of planar flux sensors mounted at the opposite end of yoke pair 410. Alternatively, a flux differential signal from both sensor pairs may be combined to produce a stronger flux differential signal output.

In the example embodiment illustrated in FIG. 4, each magnetic yoke of a yoke pair 401 of the differential probe of the present invention may be constructed of a solid ferromagnetic material or, alternatively, may comprise multiple laminations of a ferromagnetic material or powder iron. Each magnetic yoke of yoke pair 401 is of a general U-shaped structure having a pair of arm portions ending in a flat core-facing flux-injecting surface. Although the differential probe of the present invention may consist of a plurality of flux-inducing yoke pairs of various structures and arrangements, in the example preferred embodiment described herein, the differential probe comprises a single yoke pair, 401, wherein each yoke is substantially U-shaped, basically identical and maintained in a fixed, closely spaced relationship to the other yoke comprising the pair.

Figure 5:
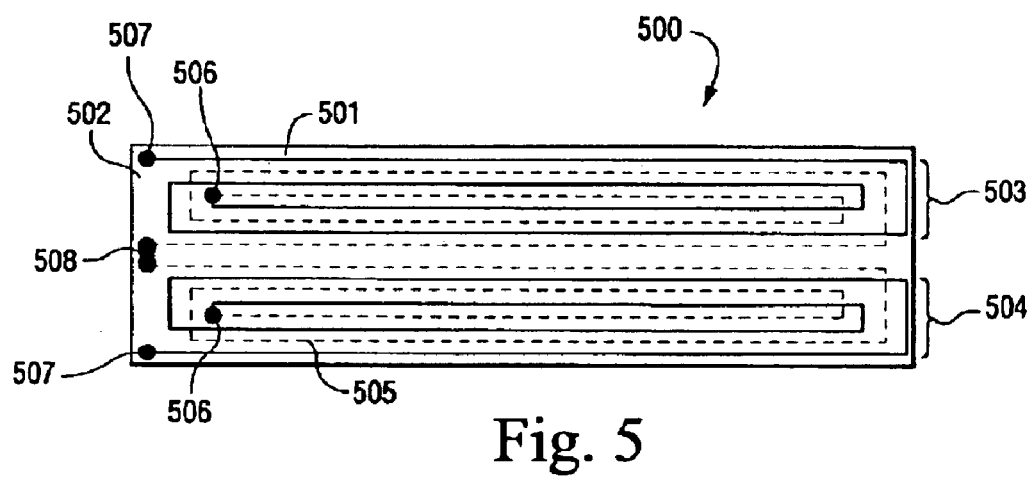
FIG. 5 is a bottom view of one example embodiment of a flux sensing coil for use with the present invention.

FIG. 5 shows an alternative example embodiment of the differential flux sensor coil arrangement 426/428 of FIG. 4. In the FIG. 5 example, coil windings 500 are conductive traces printed on the surface of a thin non-conductive substrate 502 such as, for example, Mylar™ Planar flux sensor 500 consists of two identical coils, 503 and 504, that are connected in a series-bucking relationship. In this example, only one sensor yoke is required. The differential flux sensing system is located entirely on one surface of one arm (or both arms to increase signal magnitude). Solid lines 501 indicate conductive traces on a top surface of substrate 502 and dashed lines 505 indicate conductive traces on the opposite or bottom surface of substrate 502. Feed-through holes 506 allow conductive traces on one surface of substrate 502 to be connected to conductive traces on the opposite side. Conductive pads 507 or other conductive terminals may be employed for connecting flux sensor 500 electrically to another similar flux sensor or other external components. Conductive strip 508 connects coils 503 and 504 electrically in series.

Figure 6:
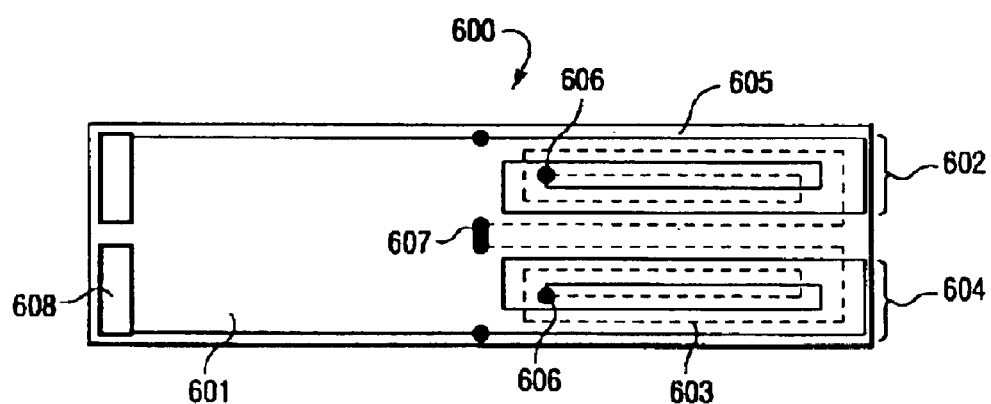
FIG. 6 is a bottom view of another embodiment of a flux sensing coil for use with the differential probe of the present invention.

FIG. 6 shows an example alternative embodiment of the differential flux sensor 500 of FIG. 5. In this example, a planar flux sensor 600 is formed having two surface coils 602 and 604 which extend the width of a core tooth. Each coil is formed as an electrically conductive trace pattern on the surface of the thin non-conductive substrate 601. Half of the coil windings are printed on one surface of substrate 601 as indicated by solid lines 605. The remaining half of the windings of each coil are printed on the bottom or opposing surface of substrate 601 as indicated by dashed line 603. Conductive feed-throughs 606 connect the windings on each side of the substrate together and conductive strip 607 connects coils 602 and 604 electrically in series. The conductive traces forming in the windings of coils 602 and 604 are configured such that coil 602 is parallel and in a magnetically bucking configuration with respect to coil 604. Electrically conducting traces 605 are brought out to conductive pads 608 for convenient connection to external devices.

Although the two example embodiments for a planar flux sensor illustrated in FIGS. 5 and 6 are shown with only two coil winding turns per coil on each side of the insulating substrate, additional coil windings could be fabricated on each side depending on the width of the conductive trace and separation of adjacent conductors. Various alternative embodiments of the planar coil are also considered, such as, for example, an embodiment having both coils fabricated on only one side of the underlying substrate.

In the example flux sensor embodiments of FIGS. 5 and 6, the length of the planar flux sensor including the etched conductive-trace coil is preferably substantially the entire width of the stator core tooth surface of the machine under test. On the other hand, the width of the flux sensor, including its etched conductive-trace coil windings, may be made as small as the thickness of two or more core laminations. In such case, each coil of the flux sensor would have a width on the order of the thickness of a single lamination.

Figure 7:
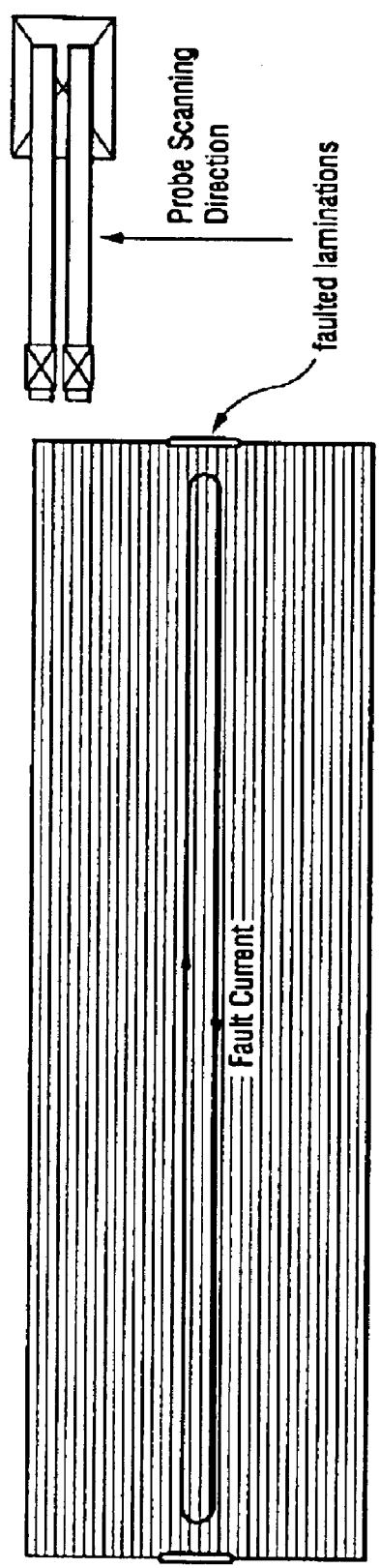
FIG. 7 is a cut-away side-view diagram illustrating a testing arrangement wherein the differential probe of the present invention is scanned across the core laminations for detecting faults.

FIG. 7 shows an example core lamination testing arrangement wherein the differential probe of the present invention is scanned across multiple laminations of a laminated core to detect inter-lamination faults. Regardless of which of the one or more flux sensor embodiments is used, measurements are performed, for example, by axially moving the differential probe relative to core teeth, supplying current to the probe excitation windings, measuring the resulting flux difference signal from a pair of adjacent flux sensors along the same tooth and analyzing the computed signal to detect a core fault such as shorted laminations. Preferably, measurements are made until all regions of the core have been tested.

Figure 8:
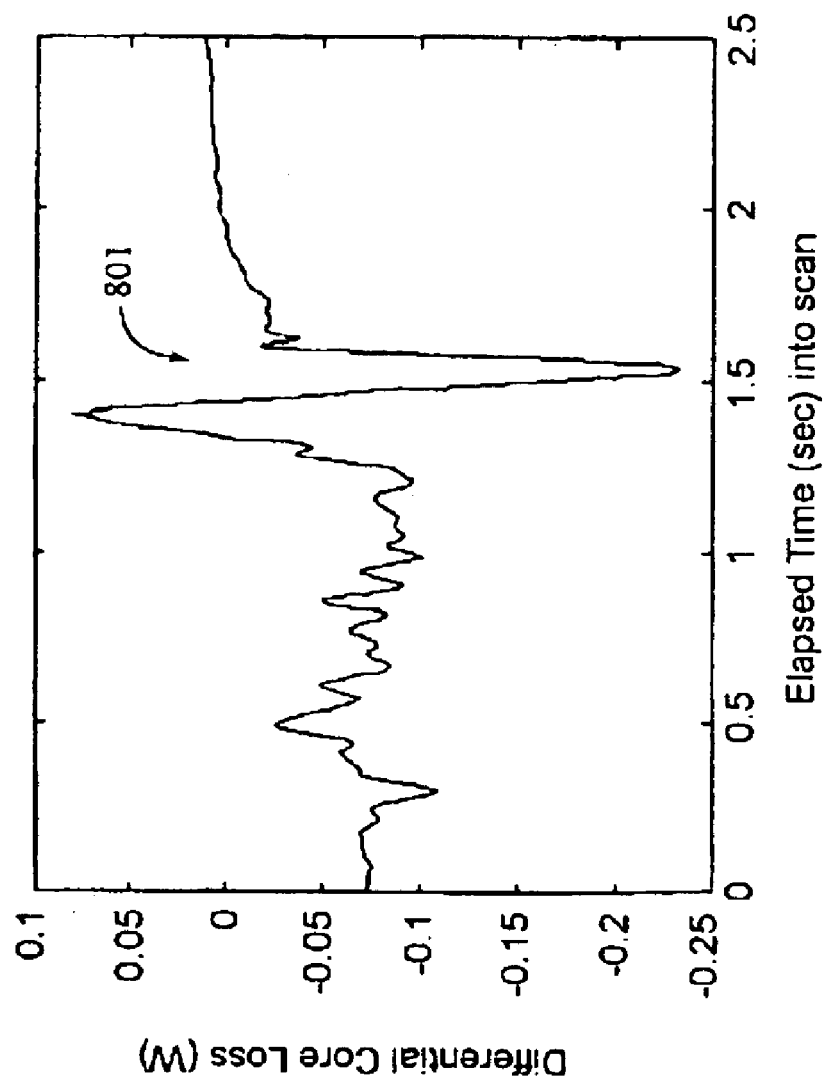
FIG. 8 is a graph illustrating an example of differentially measured incremental stator core losses measured during a scanning test of a faulted core tooth pair.

FIG. 8 shows a graph of one example of differential core losses measured using the present invention during a scanning test along a core tooth pair. The measured fluctuation 801 in detected magnetic power is indicative of core losses due to a lamination fault in the core located at the position of the probe corresponding to it position at 1.4–1.5 seconds into a testing scan.

Figure 9:
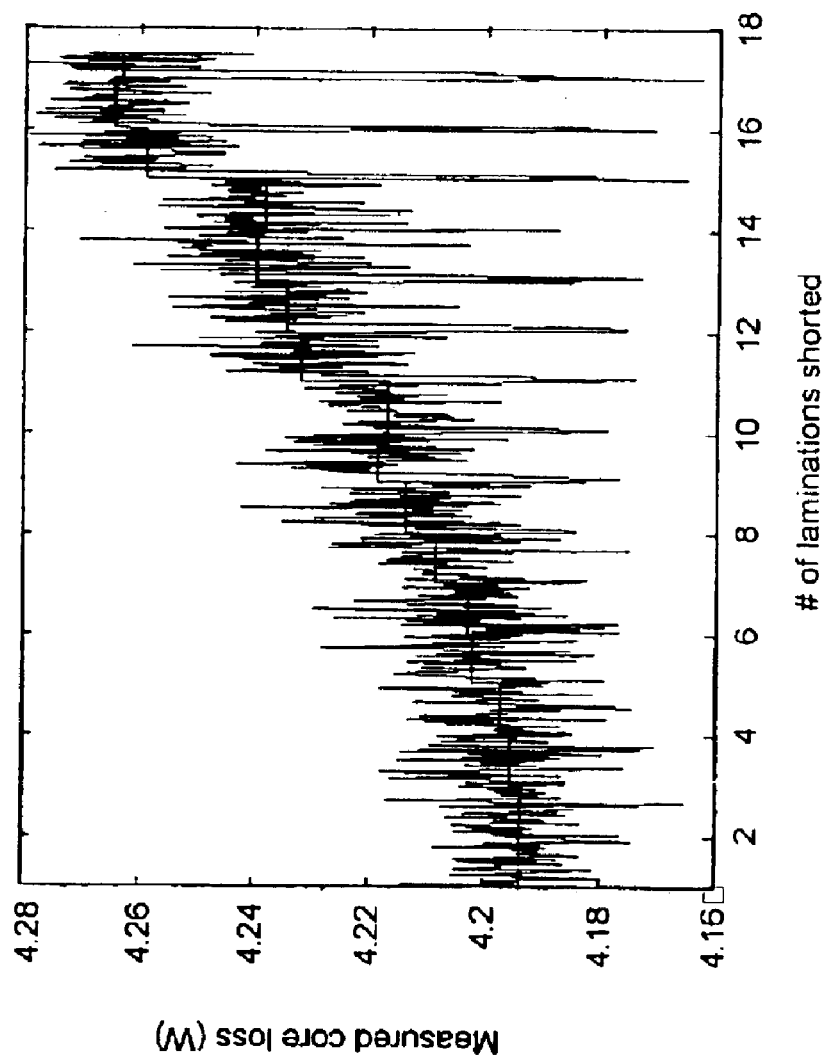
FIG. 9 is an example graph illustrating measured total core loss as a function of the number of laminations shorted.

FIG. 9 shows some experimental results of a general flux injection fault test conducted using a single yoke non-differential type probe. The graph of FIG. 9 illustrates core loss (in Watts) as a function of the number of shorted laminations. As can be seen in FIG. 9, detecting a variation in the injected magnetic flux due to the presence of a fault in core laminations when using a single yoke (non-differential) type flux-injection test probe requires detecting a very small change in a large signal in the presence of much background signal "noise". Since the signal-to-noise ratio is very low, a high resolution measurement is required to detect the small changes in the injected magnetic flux. In contrast, if the dual yoke differential probe of the present invention is used, only flux signal differences are measured and background noise signals are effectively cancelled-out or nulled.

Figure 10:
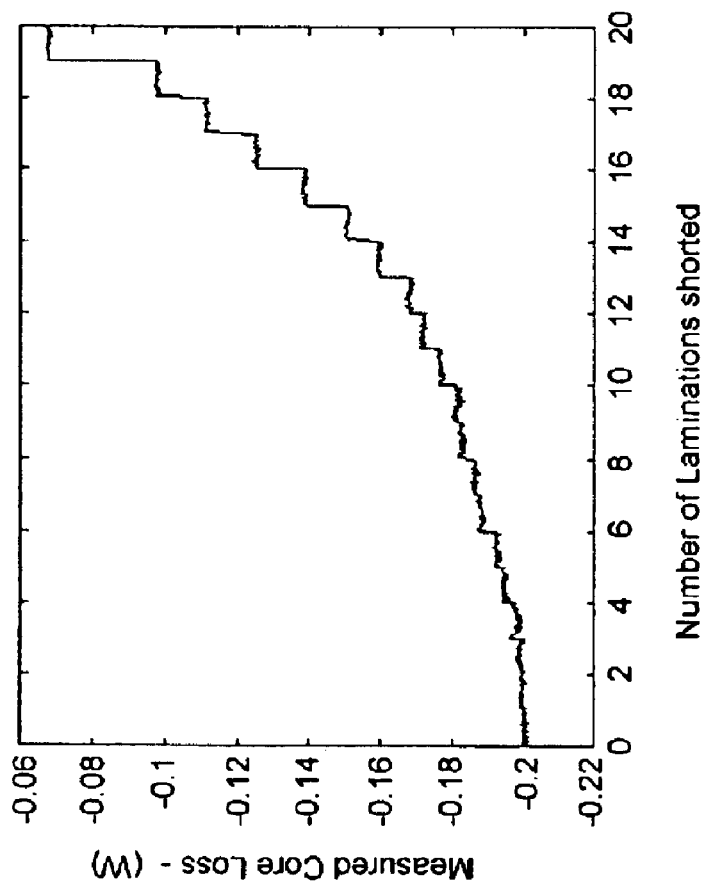
FIG. 10 is a graph illustrating an example of the core losses measured using the differential probe of the present invention.

FIG. 10 shows example results of a flux injection fault test conducted using the dual yoke differential probe of the present invention for scanning a portion of the core. The graph illustrates measured core loss in the laminations as a function of the number of shorted laminations. As the Core Loss vs. Time Index graph of FIG. 8 indicates, the measured change in flux during a scan is essentially zero for healthy laminations (although some slight DC bias might be present due to unequal magnetic cores). Although the measured flux difference signal when using the dual yoke differential probe of the present invention is very small (assuming it is measured at the same resolution as a flux signal measured with a non-differential probe), the signal-to-noise ratio is significantly higher thus improving the chances of detecting a fault. Moreover, when using the differential probe of the present invention, a "rise-fall-fall-rise" signal pattern is observed in the Core Loss vs. Time Index graph, whereas only a "rise-fall" signal pattern would be observed if a conventional single yoke non-differential type test probe were used. This distinction further enhances the reliability of performing flux injection test measurements using the dual yoke differential probe of the present invention since the "rise-fall" type pattern produced by a single yoke non-differential type test probe may be observed during a test due to reasons other than lamination faults.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for detecting faults in a laminated core of an electric machine, comprising:
    (a) positioning a pair of magnetic flux injection yokes near at least one tooth of the core, the yokes being arranged side-by-side in close proximity to each other, each yoke having a pair of flux injecting arm portions and each yoke being wound with a magnetic flux excitation winding and having a flux sensor on at least one of the arm portions;
    (b) supplying current to the flux injection winding of at least one yoke to inject magnetic flux into the at least one tooth of the core;
    (c) measuring a flux difference signal obtained between two adjacent flux sensors, each flux sensor of the two sensors from which the difference signal is obtained being located on a different yoke; and
    (d) using the measured flux difference signal to detect a core lamination fault.

2. The method of claim 1 wherein (a) comprises positioning the pair of yokes near two teeth of the core.

3. The method of claim 2 wherein (a) comprises positioning the pair of yokes near two adjacent teeth of the core.

4. The method of claim 1 further comprising moving the pair of yokes together incrementally along two teeth across core laminations and detecting a magnetic flux differential at adjacent regions in the core.

5. The method of claim 1 wherein (d) comprises measuring a drive current supplied to the flux injection winding of at least one yoke and computing an averaged product of the drive current and the measured flux differential signal.

6. A test probe apparatus for detecting faults in a laminated core of an electric machine, comprising:
    at least two magnetic flux injection yokes arranged side-by-side in close proximity, each yoke comprising at least two arm portions having a flux-injection surface at an end of each arm, each yoke being wound with an excitation winding and at least one arm portion of each yoke having a magnetic flux sensor affixed near the flux-injection surface.

7. The test probe apparatus of claim 6, wherein the flux sensor is a conductive winding wound around a yoke arm portion near the flux injecting surface.

8. The test probe apparatus of claim 6, wherein the flux sensor is a substantially planar conductive coil located on the flux-injection surface.

9. The test probe apparatus of claim 6, wherein flux-injection surfaces of each yoke are substantially flat and the flux sensor is a planar conductive coil affixed on a flux-injection surface.

10. The test probe apparatus of claim 9, wherein the planar conductive coil has a width that is substantially equal to the width of the flux-injecting surface of a yoke arm.

11. The test probe apparatus of claim 9, wherein the planar conductive coil has a width that is substantially equal to the width of a core tooth of an electric machine.

12. The test probe apparatus of claim 9, wherein the planar conductive coil is substantially rectangular in shape.

13. The test probe apparatus of claim 6, wherein the flux sensor comprises a planar conductive coil formed on a thin non-conductive substrate.

14. The test probe apparatus of claim 13, wherein the planar conductive coil is formed half on one side of the non-conductive substrate and half on an opposite side of the non-conductive substrate.

15. A system for detecting faults in a laminated core of an electric machine, comprising:
    a flux differential detecting magnetic flux-injection test probe device, said probe injecting a magnetic flux into at least two closely spaced adjacent regions of the core and producing a flux difference signal indicative of a difference in magnetic flux detected between the two closely spaced adjacent core regions;
    a current source for supplying an electrical drive current to the probe;
    a current source sensor for detecting a driving current supplied to the probe and producing a digital signal indicative of the driving current;
    a differential flux signal detector connected to the probe for detecting the flux difference signal and producing a digital signal indicative of the flux difference; and
    a computer receiving digital signals from the differential flux signal detector and the current source sensor for using the digital signals to detect core faults.

16. A system as set forth in claim 15 wherein the magnetic flux-injection differential test probe device comprises:
    at least one pair of magnetic flux injection yokes for being positioned near at least one tooth of the core, the pair of yokes being arranged side-by-side in close proximity to each other, each yoke being wound with a magnetic flux excitation winding and each yoke having a least one pair of flux-injecting arm portions and a magnetic flux sensor affixed on at least one of the arm portions,
    wherein at least one flux sensor affixed to a first yoke of the pair is electrically connected to an adjacently positioned flux sensor affixed on a second yoke of the pair in a manner such that an output signal produced by connected flux sensors is indicative of a magnetic flux difference between adjacent regions of the core.

17. The system of claim 15 wherein the computer computes a product of the probe driving current and the flux difference signal for use in detecting core faults.

18. A method for detecting faults in a laminated core of an electric machine, comprising:
    (a) injecting a magnetic flux through at least one core tooth into a pair of closely spaced adjacent regions of the core;

(b) measuring a flux difference between said adjacent regions of the core;

(c) repeating (a) and (b) at incrementally different positions spaced along the core tooth; and (e) using flux difference measurements obtained in (b) to detect core lamination faults.

19. The method of claim 18 further comprising: providing the flux difference measurements obtained in (b) to a digital computer used for detecting core lamination faults.

20. The method of claim 19 wherein a magnetic flux-injection differential test probe device is used to generate the magnetic flux for injecting in (a), the probe device having at least one pair of magnetic flux injection yokes for positioning near at least one tooth of the core and injecting a magnetic flux into two closely spaced regions of the core.

21. The method of claim 20 wherein the probe device is supplied with an electrical current to generate a magnetic flux for injecting in (a), and further comprising:

using the computer to compute an averaged product of an amount of electrical current supplied to the probe for generating an injected magnetic flux in (a) and the flux difference measurements detected in (b), said computed product being indicative of a core fault.

* * * * *